United States Patent [19]

Steinman et al.

[11] 4,209,464
[45] Jun. 24, 1980

[54] NOVEL SYNTHESIS OF 3-AMINO-2-METHYLBENZOTRIFLUORIDE FROM N-(2-X-5-TRIFLUOROMETHYLPHENYL)-S,S-DIMETHYLSULFIMIDE

[75] Inventors: Martin Steinman, Livingston; Yee S. Wong, Belleville, both of N.J.

[73] Assignee: Schering Corporation, Kenilworth, N.J.

[21] Appl. No.: 968,649

[22] Filed: Dec. 11, 1978

Related U.S. Application Data

[63] Continuation-in-part of Ser. No. 805,492, Jun. 10, 1977, abandoned.

[51] Int. Cl.$^2$ .................. C07C 85/20; C07C 85/24; C07C 85/26
[52] U.S. Cl. .................. 260/578; 260/582; 260/551 S
[58] Field of Search .................. 260/578, 609 R

[56] References Cited

U.S. PATENT DOCUMENTS 3,894,034  7/1975  Gassman et al. ............. 260/574 X

OTHER PUBLICATIONS

Claus et al., "Tetrahedron Letters", No. 32, pp. 3607–3610 (1968).

*Primary Examiner*—John Doll
*Attorney, Agent, or Firm*—Raymond A. Mc Donald

[57] ABSTRACT

This invention relates to a novel process for preparing 3-amino-2-methylbenzotrifluoride, and to certain novel intermediates produced by the process. 3-Amino-2-methylbenzotrifluoride is a key intermediate useful in the preparation of valuable therapeutic agents such as, for example, 2-(2-methyl-3-trifluoromethyl)anilino nicotinic acid.

6 Claims, No Drawings

NOVEL SYNTHESIS OF 3-AMINO-2-METHYLBENZOTRIFLUORIDE FROM N-(2-X-5-TRIFLUOROMETHYLPHENYL)-S,S-DIMETHYLSULFIMIDE

This is a continuation in-part application of our copending application Ser. No. 805,492 filed June 10, 1977, now abandoned.

This invention relates to a novel synthesis for the preparation of certain 3-aminobenzotrifluorides. More particularly, this invention relates to a novel process wherein certain 4-substituted-3-aminobenzotrifluorides are converted to 3-amino-2-methylbenzotrifluoride using inexpensive and readily available reactants under reaction conditions which are essentially nonhazardous. Additionally, the invention relates to the novel intermediates produced by the process.

The compound, 3-amino-2-methylbenzotrifluoride is a valuable intermediate in the preparation of certain therapeutic agents. For example, U.S. Pat. No. 3,337,750 discloses that 2-(2-methyl-3-trifluoromethyl)anilino nicotinic acid is a useful therapeutic agent having valuable anti-inflammatory/analgesic properties. In U.S. Pat. No. 3,390,172, it is taught that N-(2-methyl-3-trifluoromethylphenyl)anthranilic acid is a valuable anti-inflammatory agent. In both instances, 3-amino-2-methyl-benzotrifluoride serves as a valuable intermediate.

In the prior art, U.S. Pat. No. 3,390,172 teaches the process for preparing 3-amino-2-methylbenzotrifluoride wherein 2-methyl-3-nitrobenzoic acid is treated with sulfur tetrafluodide at temperatures in excess of 100° C. in a stainless steel bomb for about 15 hours under high pressure to produce 3-nitro-2-methylbenzotrifluoride. The 3-nitro-2-methylbenzotrifluoride is chemically reduced by convention means. That process presents a significant safety hazard in that the high pressure reaction conditions could cause the reaction vessel to rupture. The probability of such a rupture is greatest when commercial quantities are being produced. Further, sulfur tetrafluoride is of limited availability and therefore is an expensive reactant adding substantially to the cost of the overall procedure.

We have now discovered a method for preparing 3-amino-2-methylbenzotrifluoride which obviates the use of high pressure and the use of scarce, expensive reactants resulting in a process which substantially reduces the cost and the hazard of producing this desired compound.

More specifically, this invention is the process for preparing 3-amino-2-methylbenzotrifluoride which comprises: (a) condensing a 3-amino-4-X-benzotrifluoride with dimethylsulfoxide in the presence of an activating agent, (b) heating the N-(2-X-5-trifluoromethylphenyl)-S,S-dimethyl sulfimide at from about 85° C. to about 200° C. and (c) chemically reducing the so-formed 3-amino-4-X-2-methylthiomethylbenzotrifluoride, wherein X is hydrogen, chloro, bromo, iodo or alkylthio.

A special agent of this invention is the unique results manifested by the Raney nickel/acetic acid reaction conditions for effecting a chemical reduction of 3-amino-4-X-2-methylthiobenzotrifluoride. In practice it is preferred to isolate the sulfimide (II) so as to minimize the risk of hydrolydid back to the aniline starting material.

The foregoing process may be depicted as follows:

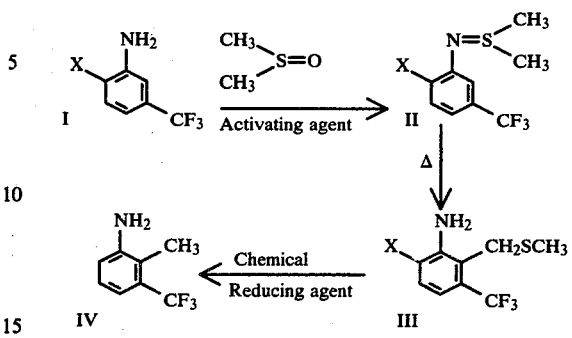

wherein X is a member selected from the group consisting of hydrogen, chloro, bromo, iodo and alkylthio.

In the first step of the process, i.e. the condensation reaction of the 3-amino-4-X-benzotrifluoride (I) with an "activated" dimethylsulfoxide, the reaction is effected by heating in a solvent an admixture of the reactants in the presence of a tertiary amine. The heating takes place at temperatures from about room temperature to about the reflux temperature of the reaction mixture, preferably at between 15° C. and 35° C. The reaction is usually permitted to proceed for about 3 to 12 hours, although 6 to 8 hours are preferred. In practice it is preferred to isolate the sulfimide (II) so as to minimize the risk of hydrolysis back to the aniline starting material. The preferred solvents for the reaction are halogenated hydrocarbons especially halogenated alkanes, such as methylene chloride, 1,2-dichloroethane, 1,3-dichloropropane and the like.

The term "activating" agent means those electrophiles which react with dimethylsulfoxide to produce a reactive sulfonium salt. Exemplary of such agents are acyl anhydrides, halogenated acyl anhydrides, dicyclohexylcarbodiimide, acyl halides, phosphorous pentoxide, polyphosphoric acid and the like. An excellent description of such agents and their use is presented by Dawson, et al. in the Journal of Organic Chemistry 42, 595 (1977).

The conversion of the sulfimides (II) to the 3-amino-4-X-2-methylthiomethylbenzotrifluoride (III) may be effected by heating the sulfimides from about 85° C. to about 200° C. This rearrangement may be effected in the absence of a solvent or in solvents such as halogenated hydrocarbons, aromatic hydrocarbons and cyclic ethers. Exemplary of such solvents are chloroform, 1,2-dichloroethane, benzene, toluene, xylene, dioxane, glyme, diglyme, triglyme and the like. The conversion is, preferably, effected in 1,2-dichloroethane in the presence of a tertiary amine (catalyst), such as triethylamine. (The presence of the catalyst permits the reaction to take place at a lower temperature.) Alternatively, a sterically hindered alcohol may be used in lieu of the tertiary amine. The term sterically hindered alcohol embraces such alcohols as t-butanol 2-phenyl-2-propanol, 1,1-diphenylethanol, triphenylmethanol, 1-adamantanol and the like. These preferred conditions permit Step A and Step B to be effected as one continuous operation. In those instances wherein X is hydrogen, there is produced, in addition to compound III, the 4-methylthiomethyl isomer thereof. Separation of compound III from its isomer is accomplished by fractional distillation. Having a substituent (X is other than hydrogen), at the 4-position of the 3-amino-benzotrifluoride (I) obviates the formation of the isomers.

The conversion of the 3-amino-4-X-2-methylthiomethylbenzotrifluorides (III) to the desired product (IV) may be effected by chemical reductive procedures known in the art. In those instances wherein the product of Step B bears an X-substituent selected from the group consisting of chloro, bromo or iodo, the reductive desulfurization is preferably effected with W-2 Raney nickel when the reaction medium has been made slightly acidic with acetic acid (6.6% acetic acid). In such instances, the basic Raney nickel is first washed to neutrality. However, a medium which is too acidic will hamper the de-halogenation. In the event it is not desired to remove a substituent located at the 4-position of the compounds of formula III or when it does not contain a substituent (i.e., X is hydrogen), then the chemical reaction may be conducted so that only the desulfurization reaction is preferably effected with zinc in acetic acid. The term chemical reducing agent as used herein embraces such reducing agents or combination of agents as lithium aluminum hydride in combination with zinc chloride, Hopkins reagent (10% $HgSO_4$ in aqueous $H_2SO_4$), nickel boride, aluminum amalgam, Raney cobalt, lithium or sodium metal in ammonia, Raney nickel, especially W-2 Raney nickel. The reduction is preferably performed in water or water miscible organic solvents such as dimethylformamide, tetrahydrofuran, dioxane, or alcohols including diols, such as ethylene glycol. The preferred solvents are water and lower molecular weight alcohols, such as methanol. The reaction is permitted to proceed for from about 1 to about 6 hours, i.e., until desulfurization is complete. The reaction may be effected at a temperature between ambient and the reflux temperature of the reaction mixture, preferably at about 60° C. to 75° C.

The novel compounds of this invention are those of the formula:

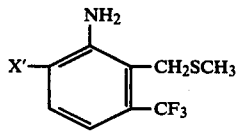

V wherein X' is selected from the group consisting of chloro, bromo, iodo and alkylthio, said alkyl group having 1 to 8 carbon atoms.

The following examples set forth the best mode known to us for practicing this invention. However, they should not be construed as limiting the scope thereof.

EXAMPLE 1

3-Amino-2-Methylbenzotrifluoride

A. N-(3-trifluoromethyl)phenyl-S,S-dimethylsulfimide

Add 426 g. of phosporous pentoxide (3 moles) to 1.0 liter of 1,2-dichloroethane in a 5 liter, 3 necked-round bottom flask equipped with reflux condenser, mechanical stirrer, thermometer and dropping funnel with a nitrogen inlet. Cool the resulting suspension in an ice bath, add 450 ml. of dimethylsulfoxide (6 moles), in a dropwise fashion, and, with constant stirring, maintain the temperature at 15° C.-25° C. Add a solution of 322 g. of m-aminobenzotrifluoride (2 moles) in 708 g. of triethylamine (dropwise) over 2 hours keeping the temperature below 25° C. Stir for another hour, heat to 30° C. and maintain at 30° C.-35° C. for 4 hours. Cool in an ice bath.

B. 3-amino-2-methylthiomethylbenzotrifluoride

Add a mixture of 200 ml t-butyl alcohol and 25 ml. of 1,2-dichloroethane to the cooled product of Part A and then heat the mixture to 85° C.-95° C. and maintain the resulting mixture at this temperature for about 16 hours. Cool the mixture to room temperature, pour onto a mixture of 120 g. of sodium hydroxide in water and 3 kg. of ice. Collect the organic layer. Wash with 10% sodium hydroxide and then twice with water. Remove the organic solvent and distill at 2 mm, 75° C.-95° C., to yield the mixture of 3-amino-2-methylthiomethylbenzotrifluoride and 3-amino-4-methylthiomethylbenzotrifluoride. Separate the isomeric mixture by fractional distillation through a packed column in vacuo and obtain thereby 3-amino-2-methylthiomethylbenzotrifluoride boiling at 83° C. (2 mm) and 3-amino-4-methylthiomethylbenzotrifluoride boiling at 90° C. (2 mm).

C. 3-amino-2-methylbenzotrifluoride

Wash 5 to 10 teaspoonfuls of W-2 Raney nickel catalyst with distilled water to neutrality, then three times with absolute alcohol. Dissolve 10 g. of 3-amino-2-methylthiomethylbenzotrifluoride in 100 ml. of methanol and add 4 teaspoonfuls of the washed W-2 Raney nickel. Reflux for 4 hours, filter to remove the catalyst and evaporate the solvent in vacuo to yield the title compound.

Alternatively, the 3-amino-2-methylthiomethylbenzotrifluoride may be chemically reduced by the following technique.

C'. 3-amino-2-methylbenzotrifluoride

Stir a mixture of 5 g. of 3-amino-2-methylthiomethylbenzotrifluoride, 12.5 ml of isopropanol, 15 g. of zinc powder and 2.5 ml of water in a 500 ml, 3-necked round bottom flask fitted with mechanical stirrer, dropping funnel with a nitrogen inlet, and reflux condenser with Clorox trap, and bubble-counter. Immerse the flask in an oil bath at 80° C. Slowly add a solution of 30 ml of water and 15 ml of acetic acid to the well-stirred mixture via the dropping funnel (about 2.5 ml per portion and 20 minutes for each portion). Stir the reaction mixture at 80° C. and cool the reaction mixture. Add 50 ml of water and extract three times with hexane. Dry the combined organic extracts and evaporate to yield the title compound which may be steam distilled for further purification.

EXAMPLE 2

3-Amino-2-Methylbenzotrifluoride

A. N-(2-chloro-5-trifluoromethyl)phenyl-S,S-dimethylsulfimide

Add 106 g. of phosphorous pentoxide to 250 ml. of 1,2-dichloroethane in a 1 liter, 3-necked round bottom flask equipped with reflux condenser, mechanical stirrer, thermometer and dropping funnel with a nitrogen inlet. Cool in an ice bath. Add 112 ml. of dimethylsulfoxide dropwise to the well-stirred suspension. Maintain at 15° C.-25° C. with cooling. Add a solution of 98 g. of 3-amino-4-chlorobenzotrifluoride in 177 g. of triethylamine dropwise over 2 hours keeping the temperature below 25° C. Stir for another hour, then heat to 30° C.

and maintain at 30° C.–35° C. for 4 hours. Cool in an ice bath.

B.
3-amino-4-chloro-2-methylthiomethylbenzotrifluoride

Add a mixture of 50 ml of t-butyl alcohol and 6 ml. of 1,2-dichloroethane to the cooled product of A (above) and then heat the mixture to 85° C.–95° C. Maintain at this temperature for about 16 hours. Cool the mixture to room temperature, pour onto a mixture of 30 g. of sodium hydroxide in water and 1 kg. of ice. Collect the organic layer. Extract the aqueous layer with a mixture of toluene and hexane and combine with the organic layer. Wash with 10% sodium hydroxide and then twice with water. Remove the organic solvent and distill through a packed column to obtain thereby the product of this step boiling at 79° C.–85° C. (2 mm).

Alternatively, the 3-amino-4-chlorobenzotrifluoride may be replaced with equivalent quantities of 3-amino-4-bromobenzotrifluoride, 3-amino-4-iodobenzotrifluoride, 3-amino-4-methylthiobenzotrifluoride, 3-amino-ethylthiobenzotrifluoride, 3-amino-4-n-propylthiobenzotrifluoride, 3-amino-4-n-butylthiobenzotrifluoride, 3-amino-4-heptylthiobenzotrifluoride or 3-amino-4-octylthiobenzotrifluoride, and by following substantially the teachings of Parts A and B of this example, there is produced the following: 3-amino-4-bromo-2-methylthiomethylbenzotrifluoride, 3-amino-4-iodo-2-methylthiomethylbenzotrifluoride, 3-amino-4-methylthio-2-methylthiomethylbenzotrifluoride, 3-amino-4-ethylthio-2-methylthiomethylbenzotrifluoride, 3-amino-4-n-propyl-2-methylthiomethylbenzotrifluoride, 3-amino-4-n-butyl-2-methylthiomethylbenzotrifluoride, 3-amino-4-heptylthio-2-methylthiomethylbenzotrifluoride and 3-amino-4-octylthio-2-methylthiomethylbenzotrifluoride.

C. 3-amino-2-methylbenzotrifluoride

Dissolve 2 g. of 3-amino-4-chloro-2-methylthiomethylbenzotrifluoride in 50 ml. of 90% ethanol which is 1 N in potassium hydroxide. Add 2 teaspoonfuls of Raney nickel (W-2). Stir at 70° C. for 3 hours, cool and filter. Add 50 ml. of water and extract three times with hexane. Dry and evaporate the combined organic extracts to yield the title compound.

Similarly, the 3-amino-4-chloro-2-methylthiomethylbenzotrifluoride may be replaced with equivalent quantities of 3-amino-4-bromo-2-methylthiomethylbenzotrifluoride, 3-amino-4-iodo-2-methylthiomethylbenzotrifluoride, 3-amino-4-methyl-2-methylthiomethylbenzotrifluoride, 3-amino-4-ethylthio-2-methylthiobenzotrifluoride, 3-amino-4-n-propylthio-2-methylthiomethylbenzotrifluoride, 3-amino-4-n-butylthio-2-methylthiomethylbenzotrifluoride, 3-amino-4-heptylthio-2-methylthiomethylbenzotrifluoride, or 3-amino-4-octylthio-2-methylthiomethylbenzotrifluoride, and by following substantially the teachings of Step C of this example, there is produced 3-amino-2-methylbenzotrifluoride.

EXAMPLE 3
3-Amino-2-Methylbenzotrifluoride

A.
N-(2-chloro-5-trifluoromethyl)phenyl-S,S-dimethylsulfimide

Add 34.5 g. of oxalyl chloride (0.27 moles) to 600 ml of methylene chloride contained in a 1 liter, 3-necked round bottom flask which is equipped with a mechanical stirrer, a thermometer, a nitrogen inlet tube and a dropping funnel with a calcium sulfate drying tube. Cool the solution in a dry-ice acetone bath. Add 39 g. of dimethylsulfoxide (0.5 moles) dropwise to the well-stirred solution at −40° to −50° C. Add 49 g. of 3-amino-4-chlorobenzotrifluoride (0.25 moles) followed by the dropwise addition of 150 ml. of triethylamine and keep the temperature at about −40° C. for two hours. Remove the dry-ice bath. Allow the reaction mixture to warm to room temperature, then warm the mixture slowly to 50° C. and maintain this temperature overnight (16 hours). Cool the mixture, then pour it onto a stirred saturated sodium chloride solution. Separate the organic layer, then concentrate it under vacuum to a residue. Dissolve the residue in toluene. Wash the solution first with 0.5% sodium hydroxide solution, then with saturated sodium chloride solution and then finally with water. Dry the organic layer over anhydrous sodium sulfate. Filter the solution and concentrate under vacuum to a residue with a bath temperature of about 50° C. Crystallize the residue from ether-hexane to obtain the title compound, m.p. 93° C.–94° C.

B. 3-amino-4-chloro-2-methylthiobenzotrifluoride

Add a mixture of 50 ml of t-butyl alcohol and 6 ml of 1,2-dichloroethane to the cooled product of A (above) and then heat the mixture to 85° C.–95° C. Maintain at this temperature for about 16 hours. Cool the mixture to room temperature, pour onto a mixture of 30 g. of sodium hydroxide in water and 1 kg. of ice. Collect the organic layer. Extract the aqueous layer with a mixture of toluene and hexane and combine with the organic layer. Wash with 10% sodium hydroxide and then twice with water. Remove the organic solvent and distill through a packed column to obtain thereby the product of this step boiling 79° C.–85° C. (2 mm).

C. 3-amino-2-methylbenzotrifluoride

Add 70 ml of water, 150 ml of glacial acetic acid and 100 g. of 3-amino-4-chloro-2-methylthiomethylbenzotrifluoride to a three-necked round bottom flask fitted with mechanical stirrer and condenser. Then add 535 g. of washed and neutralized Raney active nickel catalyst (Grace no. 28 in water). Heat to reflux (98° C.–100° C.) for 20 hours. Steam distill to obtain the title compound.

The so-produced 3-amino-2-methylbenzotrifluoride may be converted to the desired therapeutic agents by the procedures set forth in the above cited U.S. patents and by techniques well known in the art.

We claim:
1. A process for preparing a 3-amino-2-methylbenzotrifluoride which comprises the steps:
    (a) condensing a 3-amino-4-X-benzotrifluoride with an activated dimethylsulfoxide to produce the corresponding N-(2-X-5-trifluoromethylphenyl)-S,S-dimethylsulfimde,
    (b) effecting a chemical rearrangement by heating said dimethylsulfimide to form the corresponding 3-amino-4-X-2-methylthiomethylbenzotrifluoride, and
    (c) effecting the desulfurization and elimination of the 4-position substituent by chemical reductive means, said X being a member of the group consisting of, chloro, bromo, iodo and alkylthio, said alkyl moiety containing 1 to 8 carbon atoms.

2. The process of claim 1 wherein the activated dimethylsulfoxide of step (a) is obtained with phosphorous pentoxide as the activating agent.

3. The process of claim 1 wherein the chemical reducing agent of step (c) is Raney nickel.

4. The process of claim 3 wherein the reaction takes place in a slightly acidic reaction environment, said acidity being achieved with acetic acid.

5. A process for preparing 3-amino-2-methylbenzotrifluoride which comprises chemically reducing a 3-amino-4-X'-substituted-2-methylthiomethylbenzotrifluoride, said chemical reduction being effected with Raney nickel in a slightly acidic reaction environment, X' being a member of the group consisting of chloro, bromo, iodo or alkylthio, said alkyl moiety having 1–8 carbon atoms.

6. A process of claim 5 wherein said slightly acidic reaction environment has been achieved with the use of acetic acid.